US009801612B2

(12) United States Patent
Satoh

(10) Patent No.: US 9,801,612 B2
(45) Date of Patent: Oct. 31, 2017

(54) ULTRASOUND DIAGNOSTIC APPARATUS

(71) Applicant: FUJIFILM CORPORATION, Tokyo (JP)

(72) Inventor: Yoshiaki Satoh, Ashigarakami-gun (JP)

(73) Assignee: FUJIFILM CORPORATION, Tokyo (JP)

( * ) Notice: Subject to any disclaimer, the term of this patent is extended or adjusted under 35 U.S.C. 154(b) by 597 days.

(21) Appl. No.: 13/758,947

(22) Filed: Feb. 4, 2013

(65) Prior Publication Data

US 2013/0150723 A1  Jun. 13, 2013

Related U.S. Application Data

(63) Continuation of application No. PCT/JP2011/065944, filed on Jul. 13, 2011.

(30) Foreign Application Priority Data

Sep. 6, 2010 (JP) .................................. 2010-198566

(51) Int. Cl.
*A61B 8/00* (2006.01)
*G01S 7/52* (2006.01)
(Continued)

(52) U.S. Cl.
CPC .......... *A61B 8/4472* (2013.01); *A61B 8/4411* (2013.01); *A61B 8/4477* (2013.01);
(Continued)

(58) Field of Classification Search
CPC .... A61B 8/00; A61B 8/02; A61B 8/06; A61B 8/12; H03D 3/00
See application file for complete search history.

(56) References Cited

U.S. PATENT DOCUMENTS 4,819,652 A * 4/1989 Micco ...................... A61B 8/06
600/455
5,475,307 A * 12/1995 Silvian ......................... 329/300
(Continued)

FOREIGN PATENT DOCUMENTS

| JP | 11-276478 A | 10/1999 |
| JP | 2003-190159 A | 7/2003 |

(Continued)

OTHER PUBLICATIONS

Notification of Reason(s) for Refusal dated Apr. 8, 2014, with partial English translation.
(Continued)

*Primary Examiner* — James Kish
(74) *Attorney, Agent, or Firm* — McGinn IP Law Group, PLLC

(57) ABSTRACT

An ultrasound diagnostic apparatus includes an ultrasound probe including a transducer array, and a back unit connected to the ultrasound probe by wireless communication and generating an ultrasound image based on reception signals outputted from the transducer array, the ultrasound probe including a middle unit connected to the back unit by wireless communication and a front unit detachably connected to the middle unit and including the transducer array, and the front unit having a transmission driver that supplies drive signals to the transducer array and causes the transducer array to transmit an ultrasonic beam and a preamplifier that amplifies reception signals outputted from the transducer array.

13 Claims, 6 Drawing Sheets

(51) Int. Cl.
*G01S 7/00* (2006.01)
*G01S 15/89* (2006.01)

(52) U.S. Cl.
CPC ........... *G01S 7/5208* (2013.01); *A61B 8/4494* (2013.01); *G01S 7/003* (2013.01); *G01S 7/52082* (2013.01); *G01S 7/52098* (2013.01); *G01S 15/8913* (2013.01); *G01S 15/8915* (2013.01)

(56) References Cited

U.S. PATENT DOCUMENTS

| | | | | |
|---|---|---|---|---|
| 5,724,976 | A * | 3/1998 | Mine | B06B 1/0614 600/459 |
| 6,251,073 | B1 * | 6/2001 | Imran | A61B 8/4427 600/443 |
| 2002/0016545 | A1 * | 2/2002 | Quistgaard | A61B 5/0002 600/437 |
| 2003/0097071 | A1 * | 5/2003 | Halmann et al. | 600/459 |
| 2004/0002435 | A1 | 1/2004 | Petersen et al. | |
| 2005/0124890 | A1 | 6/2005 | Halmann et al. | |
| 2005/0148873 | A1 * | 7/2005 | Petersen et al. | 600/447 |
| 2009/0093719 | A1 * | 4/2009 | Pelissier | A61B 8/00 600/447 |
| 2010/0286527 | A1 * | 11/2010 | Cannon | A61B 7/04 600/459 |
| 2011/0112405 | A1 * | 5/2011 | Barthe | A45D 44/005 600/459 |
| 2011/0306886 | A1 * | 12/2011 | Daft et al. | 600/459 |

FOREIGN PATENT DOCUMENTS

| | | | |
|---|---|---|---|
| JP | 2007-111435 | A | 5/2007 |
| JP | 2007-190066 | A | 8/2007 |
| JP | 2009-060992 | A | 3/2009 |
| JP | 2009-297326 | A | 12/2009 |
| JP | 2010-374 | A | 1/2010 |
| WO | WO 2010/064156 | A1 | 6/2010 |

OTHER PUBLICATIONS

Japanese Office Action dated Jan. 7, 2014 with a partial English translation.
International Search Report (ISR) (PCT Form PCT/ISA/210) dated Aug. 23, 2011, in PCT/JP2011/065944.
PCT/IPEA/409 (International Preliminary Report on Patentability (chapter 11)), (in English), dated Mar. 21, 2013, for PCT/JP2001/065944.
PCT/IB/338, for PCT/JP2011/065944 dated Mar. 21, 2013.
Chinese Office Action dated Jul. 1, 2014, with English translation.
Extended European Search Report dated May 3, 2016.
Extended European Search Report dated Jun. 23, 2017 in European Patent Application No. 11823328.7.

* cited by examiner

ULTRASOUND DIAGNOSTIC APPARATUS

BACKGROUND OF THE INVENTION

The present invention relates to an ultrasound diagnostic apparatus and particularly to an ultrasound diagnostic apparatus permitting interchange of transducer arrays of an ultrasound probe.

Conventionally, ultrasound diagnostic apparatus using ultrasound images are employed in medicine. In general, this type of ultrasound diagnostic apparatus comprises an ultrasound probe having a built-in transducer array and an apparatus body connected to the ultrasound probe. The ultrasound probe transmits an ultrasonic wave toward a subject, receives an ultrasonic echo from the subject, and the apparatus body electrically processes reception signals to generate an ultrasound image.

In recent years, there have been developed portable ultrasound diagnostic apparatus that can be transported and placed near a bed or brought to a site where emergency medical care is needed. There have also been conceived ultrasound diagnostic apparatus having a configuration whereby the ultrasound probe and the apparatus body are connected to each other by wireless communication to improve operability. Such ultrasound diagnostic apparatus are required to be available in reduced dimensions for convenience.

Ultrasound diagnostic apparatus are used to diagnose subjects for various diagnosis purposes depending on which an appropriate frequency band may often vary. Thus, one may consider using an ultrasound probe selected according to the diagnosis purpose from a plurality of ultrasound probes having different frequency bands kept ready for use and connecting the selected probe to the apparatus body. However, because the ultrasound probes are generally expensive, keeping a plurality of ultrasound probes available for use increases the costs. Thus, there is a demand for a transducer array that is detachably provided in the ultrasound probe so that a transducer array having a suitable frequency band for the diagnosis purpose may be selected and used.

For example, Patent Literature 1 describes an ultrasound diagnostic system wherein an ultrasound probe is comprised of a transducer head containing a transducer array and a beamforming module for processing the signals from the transducer head for beamforming, and wherein the transducer head is detachably mounted to the beamforming module.

Patent Literature 2 describes an ultrasound diagnostic apparatus wherein an ultrasound probe is comprised of a transducer array and a housing for holding the transducer array, and wherein the transducer array is detachably mounted to the housing.

CITATION LIST

Patent Literature 1: JP 2003-190159 A
Patent Literature 2: JP 2009-50992 A

SUMMARY OF THE INVENTION

In the ultrasound probe of the apparatus described in Patent Literature 1, because the transducer head containing the transducer array is detachable from the beamforming module, a transducer array having an appropriate frequency band according to the diagnosis purpose can be used. However, such configuration has a problem in which the beamforming module is required to have therein mounted a broadband preamplifier with a bandwidth of, for example, about 2 to 20 MHz in order to enable operation with a plurality of transducer arrays having different frequency bands, and a pulser capable of a high drive voltage for a transducer array having a maximum drive voltage among the plurality of transducer arrays, resulting in increased dimensions of the apparatus.

Likewise, although the ultrasound probe of the apparatus described in Patent Literature 2 permits use of a transducer array having an appropriate frequency band according to the diagnosis purpose, the housing is required to have mounted therein a broadband amplifier and a high drive-voltage pulser, resulting in increased dimensions of the apparatus.

The present invention has been made to solve the above problems in the art and has an object of providing an ultrasound diagnostic apparatus permitting interchange of transducer arrays to select one having a suitable frequency band for an intended diagnosis purpose, while achieving reduction in dimensions and improvement of operability.

An ultrasound diagnostic apparatus according to the present invention comprises: an ultrasound probe including a transducer array; and a back unit connected to the ultrasound probe by wireless communication and generating an ultrasound image based on reception signals outputted from the transducer array, wherein the ultrasound probe includes a middle unit connected to the back unit by wireless communication and a front unit detachably connected to the middle unit and including the transducer array, and wherein the front unit has a transmission driver that supplies drive signals to the transducer array and causes the transducer array to transmit an ultrasonic beam and a preamplifier that amplifies reception signals outputted from the transducer array.

DETAILED DESCRIPTION OF THE INVENTION

Figure 1:
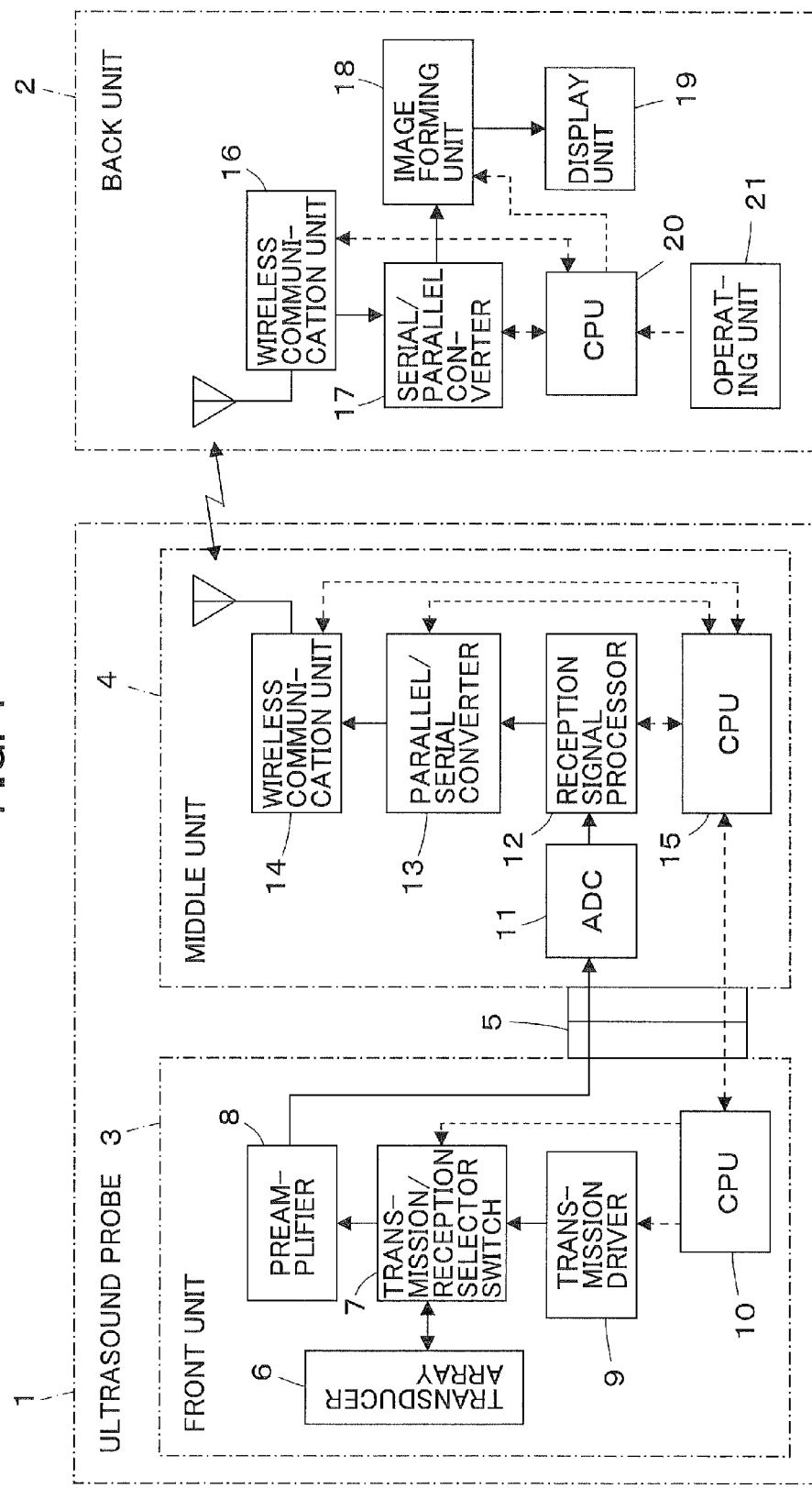
FIG. 1 is a block diagram illustrating a configuration of an ultrasound diagnostic apparatus according to Embodiment 1 of the invention.

Embodiments of the present invention will be described below based on the attached drawings.
Embodiment 1
FIG. 1 illustrates a configuration of an ultrasound diagnostic apparatus according to Embodiment 1 of the invention. The ultrasound diagnostic apparatus comprises an ultrasound probe 1 and a back unit 2 that is connected to the ultrasound probe 1 via wireless communication.

The ultrasound probe 1 comprises a front unit 3 and a middle unit 4. The front unit 3 is detachably connected via a connector 5 to the middle unit 4.

The front unit 3 comprises a one-dimensional or two-dimensional transducer array 6 including a plurality of ultrasound transducers. A preamplifier 8 and a transmission driver 9 are connected in parallel to the transducer array 6 via a transmission/reception selector switch 7. A CPU (central processing unit) 10 is connected to the transmission driver 9.

The middle unit 4 comprises an A/D converter (analog-digital converter circuit) 11 that is connected to the preamplifier 8 of the front unit 3 via the connector 5. A reception signal processor 12 is connected to the A/D converter 11, and a wireless communication unit 14 is connected to the reception signal processor 12 via a parallel/serial converter 13. A CPU 15 is connected to the reception signal processor 12 and the parallel/serial converter 13, and the CPU 15 is connected to the CPU 10 of the front unit 3 via the connector 5.

The transducers of the transducer array 6 each transmit ultrasonic waves according to drive signals supplied from the transmission driver 9 and receive ultrasonic echoes from a subject to output reception signals. Each of the transducers is constituted, for example, by a vibrator including a piezoelectric body made of a piezoelectric ceramic typified by PZT (lead zirconate titanate) or a polymeric piezoelectric element typified by PVDF (polyvinylidene fluoride) and electrodes provided on both ends of the piezoelectric body.

When the electrodes of the vibrators are supplied with a pulsed voltage or a continuous-wave voltage, the piezoelectric bodies expand and contract to cause the vibrators to produce pulsed or continuous ultrasonic waves. The ultrasonic waves are combined to form an ultrasonic beam. Upon reception of a propagating ultrasonic wave, each vibrator expands and contracts to produce an electric signal, which is then outputted as reception signal of the ultrasonic wave.

Under the control of the CPU 10, the transmission/reception selector switch 7 selectively connects the transducer array 6 to one of the preamplifier 8 and the transmission driver 9.

The preamplifier 8 amplifies the reception signals outputted from the respective channels of the ultrasonic transducers of the transducer array 6.

The transmission driver 9 comprises, for example, a plurality of pulse generators and adjusts the delay amounts of drive signals for the respective transducers based on a transmission delay pattern selected by the CPU 10 so that the ultrasonic waves transmitted from the transducer array 6 form a broad ultrasonic beam covering an area of a tissue in the subject and supplies the transducers of the transducer array 6 with the adjusted drive signals.

The CPU 10 controls the transmission driver 9 according to various control signals transmitted from the CPU 15 of the middle unit 4 connected via the connector 5.

The transducer array 6 has a specific frequency band and a specific drive voltage. The preamplifier 8 used has a frequency band corresponding to the frequency band of the transducer array 6. The transmission driver 9 used outputs a drive voltage corresponding to the drive voltage for the transducer array 6.

The A/D converter 11 digitizes the reception signals amplified by the preamplifier 8.

Under the control of the CPU 15, the reception signal processor 12 subjects the reception signals digitized by the A/D converter 11 to quadrature detection or quadrature sampling to produce complex baseband signals, samples the complex baseband signals to generate sample data containing information on the area of the tissue, and supplies the sample data to the parallel/serial converter 13. Otherwise, the reception signal processor 12 may generate sample data by performing data compression on the data obtained by sampling the complex baseband signals for high-efficiency coding.

The parallel/serial converter 13 converts the parallel sample data generated by the reception signal processor 12 having a plurality of channels into serial sample data.

The wireless communication unit 14 performs carrier modulation based on the serial sample data to generate transmission signals and supplies an antenna with the transmission signals so that the antenna transmits radio waves thereby to transmit the serial sample data. The modulation methods that may be employed herein include ASK (Amplitude Shift Keying), PSK (Phase Shift Keying), QPSK (Quadrature Phase Shift Keying), and 16QAM (16 Quadrature Amplitude Modulation).

The wireless communication unit 14 transmits the sample data to the back unit 2 and receives various control signals from the back unit 2 through wireless communication with the back unit 2, outputting the received control signals to the CPU 15.

Based on the control signal received from the back unit 2, the CPU 15 transmits a signal to the CPU 10 of the front unit 3 for the control of the transmission driver 9 and controls the wireless communication unit 14 so that sample data may be transmitted at a set transmission radio field intensity.

The connector 5 detachably connects the front unit 3 and the middle unit 4 and comprises a reception signal line for transmitting reception signals amplified by the preamplifier 8 of the front unit 3 to the A/D converter 11 of the middle unit 4 and a communication line for transmitting signals between the CPU 10 of the front unit 3 and the CPU 15 of the middle unit 4.

The ultrasound probe 1 includes a built-in battery, not shown, which supplies power to the circuits in the front unit 3 and the middle unit 4 in the ultrasound probe 1.

The front unit 3 of the ultrasound probe 1 illustrated in FIG. 1 is compatible with a sector scan mode.

The back unit 2 includes a wireless communication unit 16. An image forming unit 18 is connected to the wireless communication unit 16 via a serial/parallel converter 17, and a display unit 19 is connected to the image forming unit 18. A CPU 20 is connected to the wireless communication unit 16, the serial/parallel converter 17, and the image forming unit 18. Further, an operating unit 21 for an operator to perform input operations is connected to the CPU 20.

The wireless communication unit 16 transmits various control signals to the ultrasound probe 1 through wireless communication with the ultrasound probe 1. The wireless communication unit 16 demodulates the signal received by an antenna to output serial sample data.

The serial/parallel converter 17 converts the serial sample data outputted from the wireless communication unit 16 into parallel sample data.

The image forming unit 18 performs reception focusing on the sample data to generate image signals representing an ultrasound diagnostic image. The image forming unit 18 includes a phasing adder and an image processor.

The phasing adder selects one reception delay pattern from a plurality of previously stored reception delay patterns according to the reception direction that is set by the CPU 20 and, based on the selected reception delay pattern, provides a plurality of complex baseband signals represented by the sample data with their respective delays and adds them up to perform the reception focusing. This reception focusing yields a baseband signal (sound ray signal) where the ultrasonic echo is well focused.

The image processor generates a B-mode image signal, which is tomographic image information on, for example, a tissue inside the subject, according to the sound ray signal generated by the phasing adder. The image processor includes an STC (sensitivity time control) unit and a DSC (digital scan converter). The STC unit corrects the sound ray signal for the attenuation due to distance according to the depth of the reflection position of the ultrasonic wave. The DSC converts the sound ray signal corrected by the STC unit into an image signal compatible with an ordinary scanning method of television signals (raster conversion), and generates an image signal through required image processing such as gradation processing.

The display unit 19 displays an ultrasound diagnostic image based on image signals generated by the image forming unit 18 and includes a display device such as LCD.

Based on the instruction inputted by an operator from the operating unit 21, the CPU 20 controls the wireless communication unit 16 so that various control signals are transmitted at a set transmission radio field intensity, causes the image forming unit 18 to generate image signals, and causes the display unit 19 to display an ultrasound diagnostic image.

In Embodiment 1, the front unit 3 of the ultrasound probe 1 is detachably connected to the middle unit 4 via the connector 5. Thus, with a plurality of front units 3 including transducer arrays 6 having different frequency bands as well as preamplifiers 8 and transmission drivers 9 corresponding to the transducer arrays 6 available for use, a front unit 3 comprising a transducer array 6 having a suitable frequency band for an intended diagnosis purpose can be selected and connected to the middle unit 4.

Figure 2:
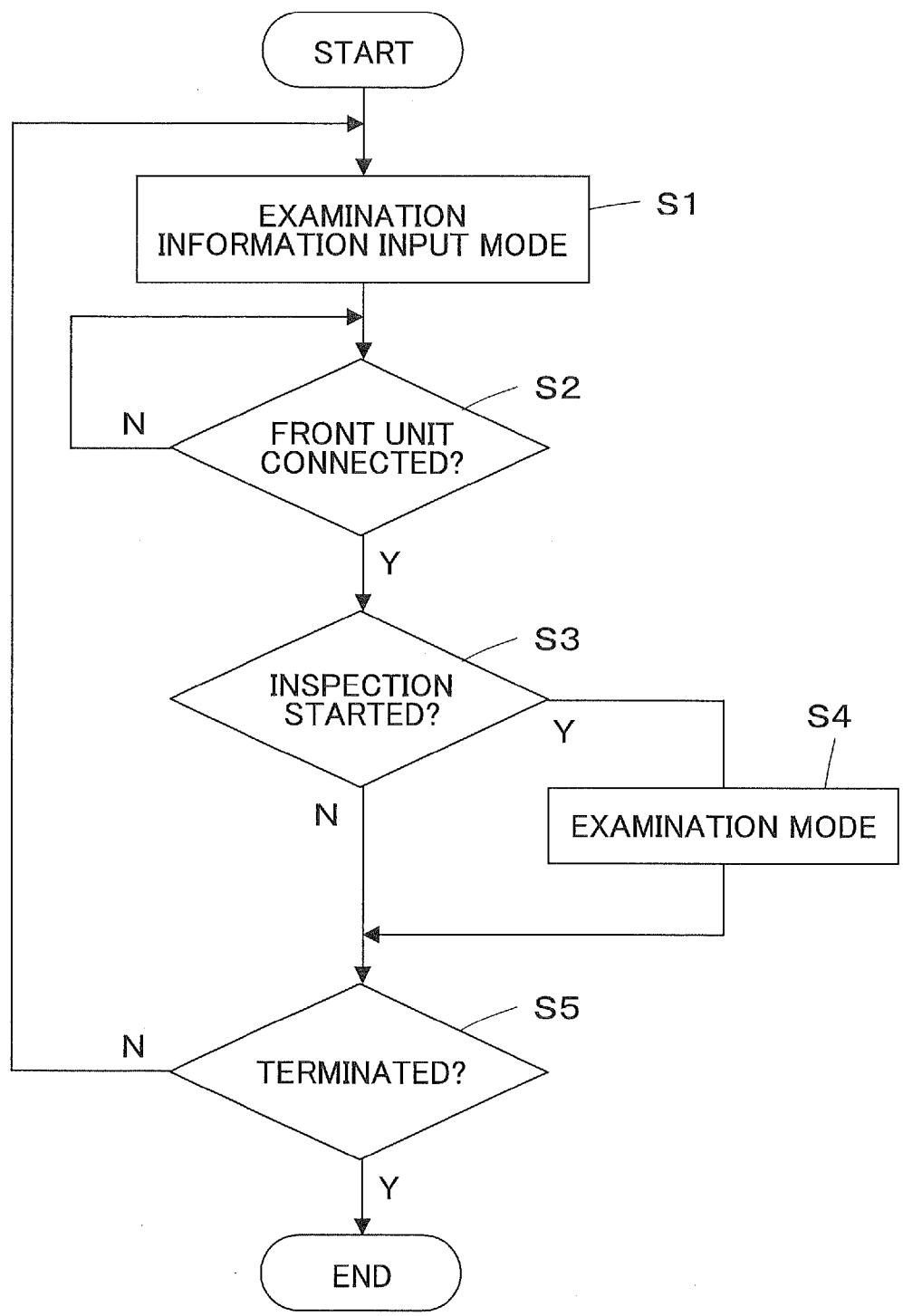
FIG. 2 is a flow chart illustrating the operation of Embodiment 1.

Next, the operation of Embodiment 1 will be described with reference to the flowchart of FIG. 2.

First, examination information including patient information and examination instructions is entered from the operating unit 21 of the back unit 2 in the examination information input mode in step S1, whereupon the CPU 20 of the back unit 2 selects one front unit 3 containing the transducer array 6 having a suitable or usable frequency band according to the entered patient information.

In step S2 to follow, the CPU 20 of the back unit 2 inquires of the CPU 15 of the middle unit 4 by wireless communication, whereupon the CPU 15 of the middle unit 4 checks with the CPU 10 of the front unit 3, so that the CPU 20 of the back unit 2 may recognize whether or not the front unit 3 selected in step S1 has been connected to the middle unit 4.

Upon recognizing that the selected front unit 3 has been connected to the middle unit 4, the CPU 20 of the back unit 2 awaits the operator's instruction to start examination in step S3 and, upon receiving the instruction to start examination, proceeds to step S4 to execute an examination mode and, in step S5, awaits the operator's instruction to terminate the examination. When instruction to terminate the examination is entered, a series of examination processes is terminated, whereas when instruction to continue the examination is entered, the CPU 20 returns to step S1 to receive examination information again.

Figure 3:
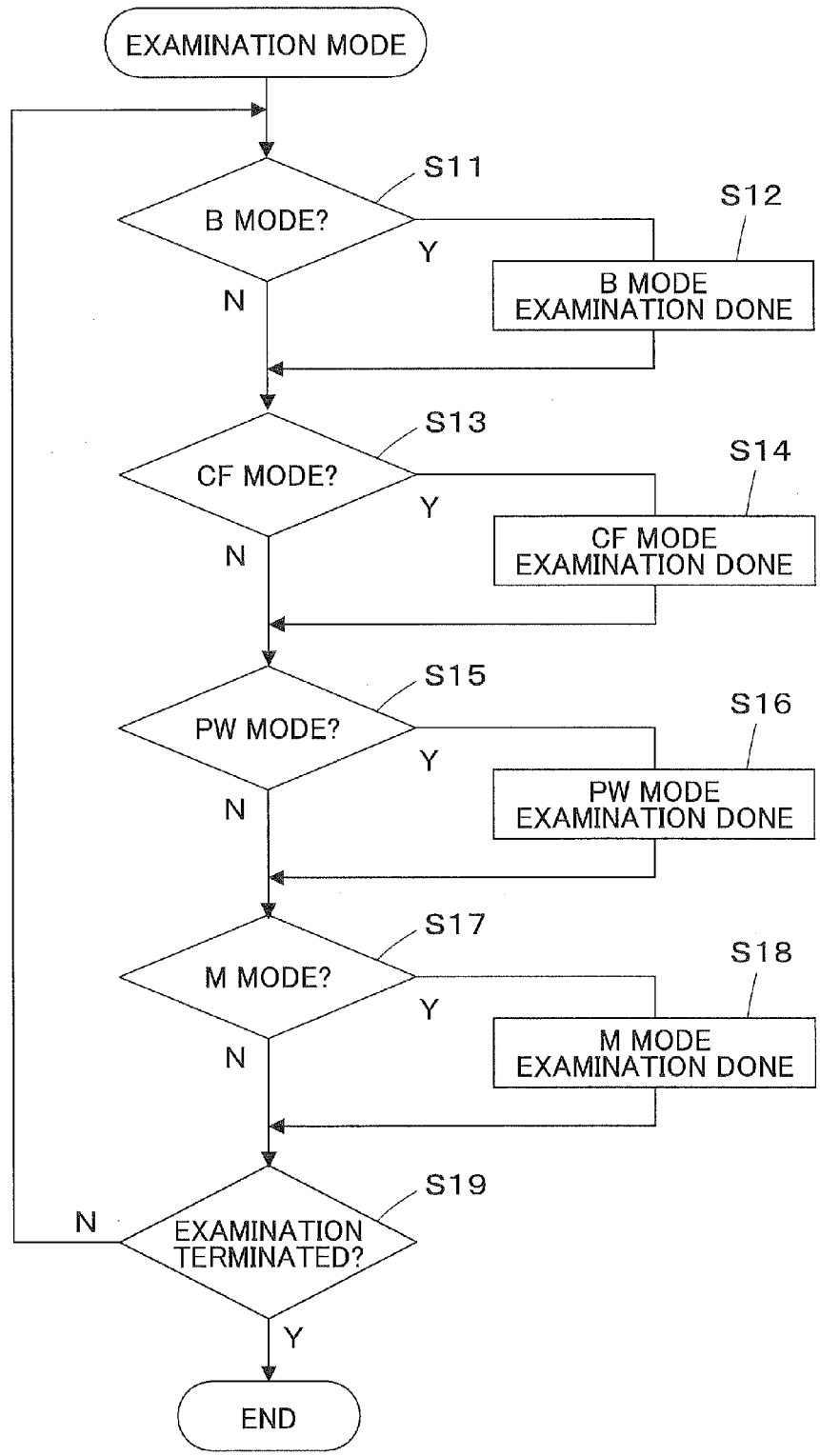
FIG. 3 is a flow chart illustrating an examination mode in Embodiment 1.

In step S4, one or more of previously set examination modes such as B mode, CF mode, PW mode, and M mode, as shown by way of example in FIG. 3, may be selected and executed. The CPU 20 of the back unit 2 checks examination information entered in step S1 to determine which mode has been designated and, upon verifying designation of B mode in step S11, proceeds to step S12 to execute examination in B mode. Upon verifying designation of CF mode in step S13, the CPU 20 proceeds to step S14 to execute examination in CF mode. Upon verifying designation of PW mode in step S15, the CPU 20 proceeds to step S16 to execute examination in PW mode. Upon verifying designation of M mode in step S17, the CPU 20 proceeds to step S18 to execute examination in M mode. When the termination of examination carried out based on the current examination information is verified in step S19, the CPU 20 proceeds to step S5 shown in FIG. 2.

The examinations in the respective modes are executed as follows.

First, operation control command is transmitted from the CPU 20 of the back unit 2 to the ultrasound probe 1 via the wireless communication unit 16. The operation control command is received by the wireless communication unit 14 of the middle unit 4 and transmitted to the CPU 15. Then, the CPU 15 outputs a command for driving the transducer array 6 to the CPU 10 of the front unit 3 via the connector 5.

The CPU 10 of the front unit 3 that received the above command operates the transmission/reception selector switch 7 to connect the transmission driver 9 to the transducer array 6, and the ultrasound transducers constituting the transducer array 6 transmit ultrasonic waves according to drive signals supplied from the transmission driver 9. Thereafter, the CPU 10 causes the transmission/reception selector switch 7 to operate so that the preamplifier 8 is now connected to the transducer array 6, and reception signals outputted respectively from the transducers of the transducer array 6 that received ultrasound echoes from a subject are amplified by the preamplifier 8 and then transmitted to the middle unit 4 via the connector 5.

The reception signals transmitted to the middle unit 4 are digitized by the A/D converter 11 and supplied to the reception signal processor 12, where sample data is generated. The sample data is serialized through the parallel/serial converter 13 and wirelessly transmitted from the wireless communication unit 14 to the back unit 2.

The sample data received by the wireless communication unit 16 of the back unit 2 is converted into parallel data through the serial/parallel converter 17, whereupon the image forming unit 18 produces an image signal appropriate for the executed examination mode, so that the display unit 19 displays an ultrasound diagnostic image based on the image signal.

As described above, the front unit 3 detachably connected to the middle unit 4 incorporates, besides the transducer array 6 having a specific frequency band, the preamplifier 8 having a frequency band corresponding to the frequency band of the transducer array 6 and the transmission driver 9 for outputting a drive voltage corresponding to the drive voltage for the transducer array 6. Thus, one need not employ an over-engineered system configuration, as conventionally required, equipped with a broadband preamplifier having a bandwidth of about, for example, 2 to 20 MHz and enabling operation with a plurality of transducer arrays having different frequency bands and a transmission driver capable of a high drive voltage adapted to a transducer array having a maximum drive voltage among a plurality of transducer arrays. Thus, a compact ultrasound diagnostic apparatus with enhanced operability can be realized.

Further, in Embodiment 1 above, the front unit 3 and the middle unit 4 are exclusively provided with the CPU 10 and the CPU 15 respectively, so that the CPU 10 controls the components in the front unit 3 while the CPU 15 controls the components in the middle unit 4. Thus, the number of control signal lines for connecting the front unit 3 and the middle unit 4 can be reduced, and both units can be detachably connected by a compact connector 5.

Embodiment 2

Although the front unit 3 of the ultrasound probe 1 used in Embodiment 1 above is compatible with a sector scan mode, the invention is not limited thereto. The front unit 3 may be compatible with other scan modes including, for example, a linear scan mode and a convex scan mode.

Figure 4:
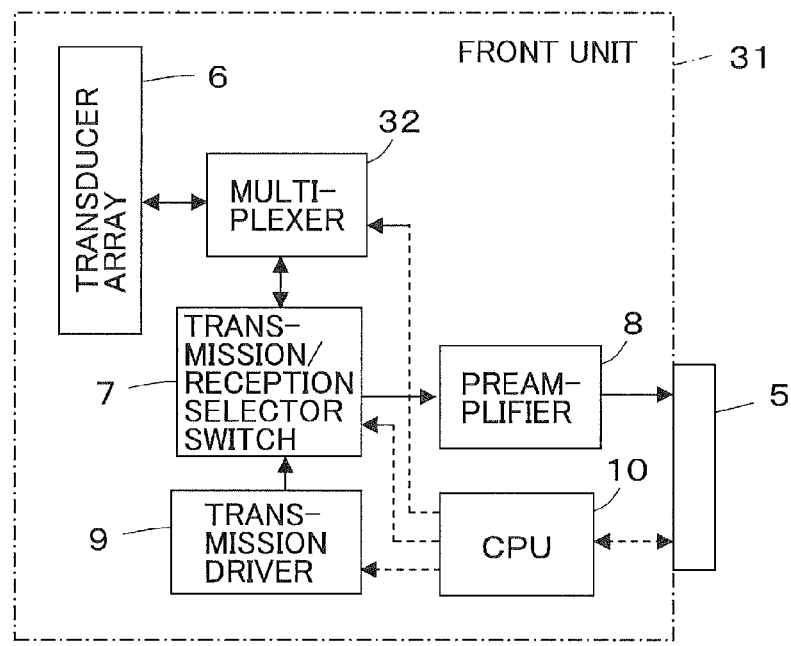
FIG. 4 is a block diagram illustrating a configuration of a front unit used in Embodiment 2.

FIG. 4 illustrates a configuration of a front unit 31 used in Embodiment 2. As compared with the front unit 3 in Embodiment 1 illustrated in FIG. 1, the front unit 31 has a multiplexer 32 connected between the transducer array 6 and the transmission/reception selector switch 7 to acquire compatibility with the linear scan mode and the convex scan mode.

Under the control of the CPU 10, some transducers among those constituting the transducer array 6 are sequentially selected and perform transmission and reception of ultrasonic waves. This enables acquisition of an ultrasound diagnostic image by the linear scan mode or the convex scan mode.

When equipped with both the front unit 3 compatible with the sector scan mode as illustrated in FIG. 1 and the front unit 31 compatible with the linear scan mode and the convex scan mode as used in Embodiment 2, one may select one of these front units according to the scan mode and connect it to the middle unit 4.

Embodiment 3

Figure 5:
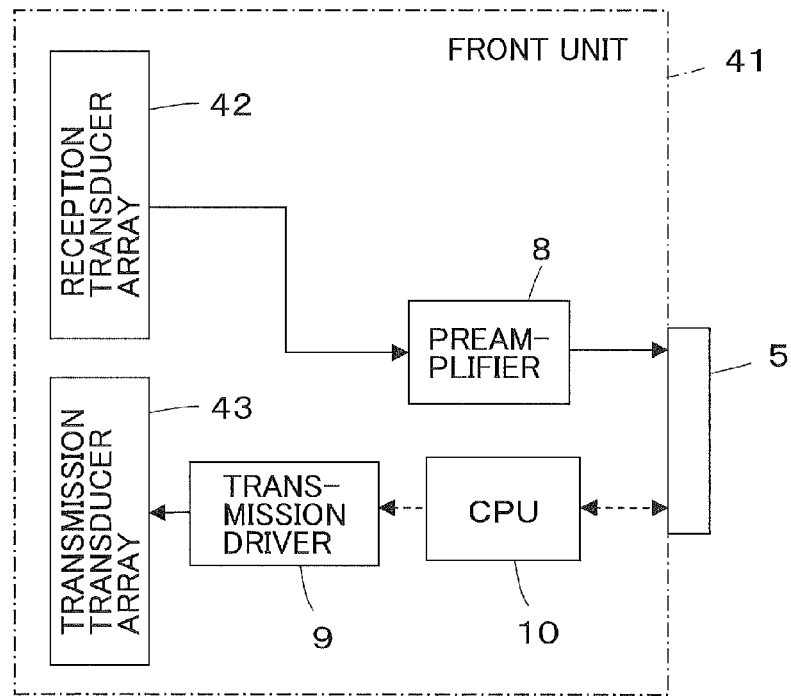
FIG. 5 is a block diagram illustrating a configuration of a front unit used in Embodiment 3.

FIG. 5 illustrates a configuration of a front unit 41 used in an ultrasound diagnostic apparatus according to Embodiment 3. As compared with the front unit 3 in Embodiment 1 illustrated in FIG. 1, the front unit 41 does not have the transmission/reception selector switch 7, and in place of the transducer array 6, has a reception transducer array 42 for only reception connected to the preamplifier 8 and a transmission transducer array 43 for only transmission connected to the transmission driver 9.

The front unit 41 is compatible with the sector scan mode.

Because the reception transducer array 42 dedicated to reception and the transmission transducer array 43 dedicated to transmission are provided, cross talk occurring in transmission of ultrasonic waves can be prevented and ultrasound diagnosis can be given with enhanced accuracy.

Figure 6:
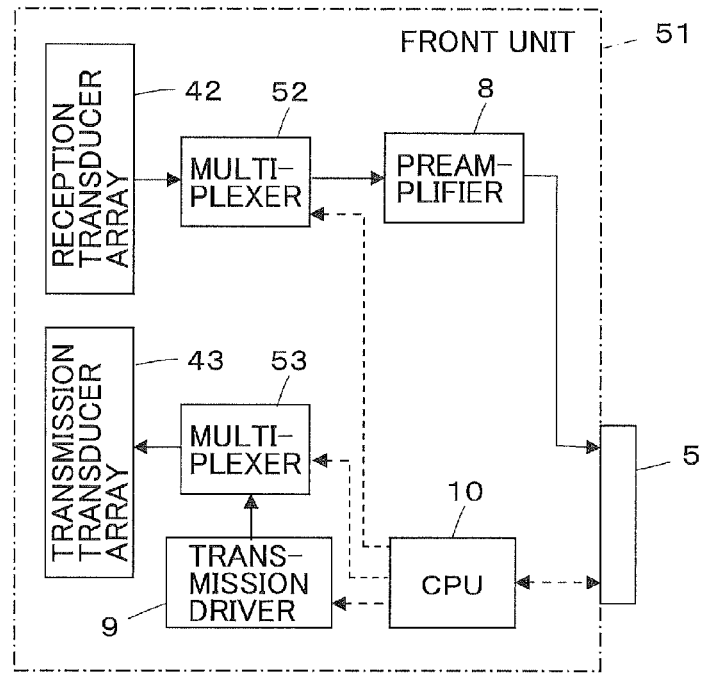
FIG. 6 is a block diagram illustrating a configuration of a front unit used in a variation of Embodiment 3.

Although the front unit 41 illustrated in FIG. 5 is compatible with the sector scan mode, the invention is not so limited; as in a front unit 51 illustrated in FIG. 6, a front unit compatible with the linear scan mode and the convex scan mode may be configured by connecting a multiplexer 52 between the reception transducer array 42 and the preamplifier 8 and connecting a multiplexer 53 between the transmission transducer array 43 and the transmission driver 9.

Embodiment 4

Figure 7:
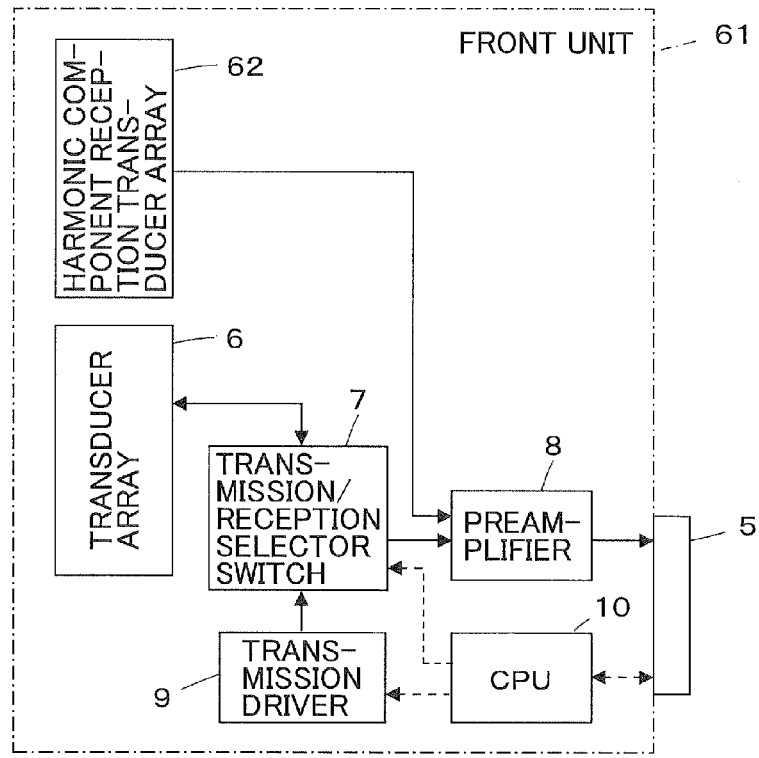
FIG. 7 is a block diagram illustrating a configuration of a front unit used in Embodiment 4.

FIG. 7 illustrates a configuration of a front unit 61 used in an ultrasound diagnostic apparatus according to Embodiment 4. As compared with the front unit 3 in Embodiment 1 illustrated in FIG. 1, the front unit 61 has a harmonic component reception transducer array 62 connected to the preamplifier 8 in addition to the transducer array 6 used for both transmission and reception.

The front unit 61 is compatible with the sector scan mode.

The harmonic component reception transducer array 62 is a transducer array having a frequency band especially adapted to harmonic components. With such a harmonic component reception transducer array 62 provided, a harmonic component can be received by the harmonic component reception transducer array 62 while an ultrasonic echo in a basic frequency band is received by the transducer array 6 that is used for both transmission and reception, enabling a still more accurate ultrasound diagnosis.

Figure 8:
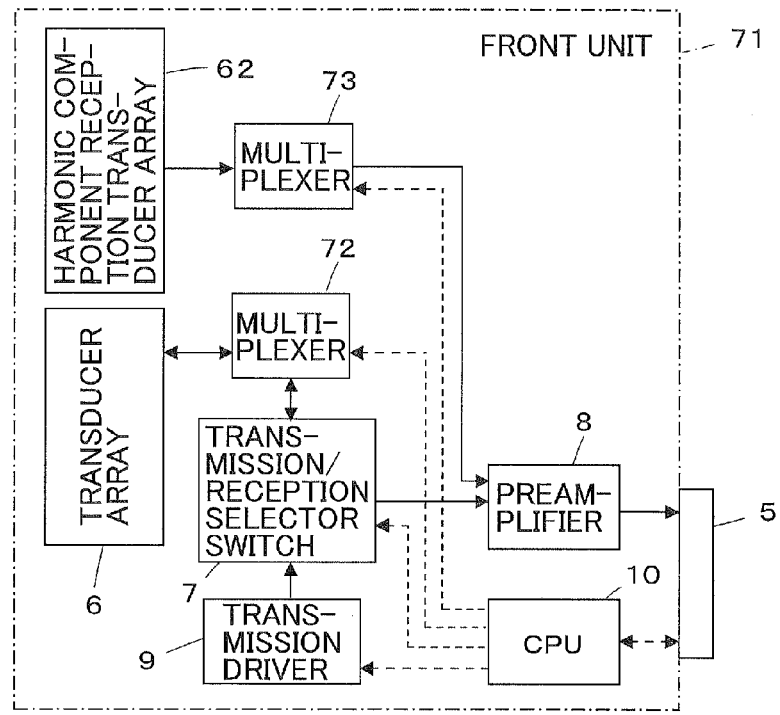
FIG. 8 is a block diagram illustrating a configuration of a front unit used in a variation of Embodiment 4.

Although the front unit 61 illustrated in FIG. 7 is compatible with the sector scan mode, the invention is not so limited; as in a front unit 71 illustrated in FIG. 8, a front unit compatible with the linear scan mode and the convex scan mode may be configured by connecting a multiplexer 72 between the transducer array 6 used for both transmission and reception and the transmission/reception selector switch 7 and connecting a multiplexer 73 between the harmonic component reception transducer array 62 and the preamplifier 8.

Embodiment 5

Figure 9:
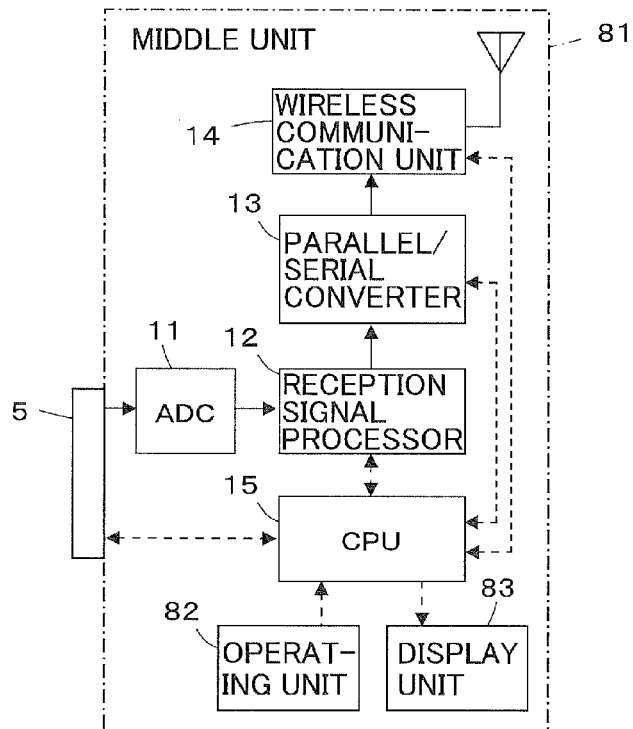
FIG. 9 is a block diagram illustrating a configuration of a middle unit used in Embodiment 5.

FIG. 9 illustrates a configuration of a middle unit 81 used in an ultrasound diagnostic apparatus according to Embodiment 5. As compared with the middle unit 4 in Embodiment 1 illustrated in FIG. 1, the middle unit 81 has an operating unit 82 for performing input operation into the ultrasound diagnostic apparatus and a display unit 83 for displaying information, both of which are connected to the CPU 15.

With the operating unit 82 provided in the middle unit 81 of the ultrasound probe 1, various kinds of information may be entered from the ultrasound probe 1 connected to the back unit 2 by wireless communication to operate the ultrasound diagnostic apparatus from the ultrasound probe 1.

Further with the display unit 83 provided in the middle unit 81 of the ultrasound probe 1, such information as a name and a kind of the front unit connected to the middle unit 81 through the connector 5 can be displayed on the ultrasound probe 1, enhancing operability and convenience.

Although Embodiment 5 includes both the operating unit 82 and the display unit 83 in the middle unit 81, only one of the operating unit 82 and the display unit 83 may be connected to the CPU 15 of the middle unit 81.

What is claimed is:

1. An ultrasound diagnostic apparatus comprising:
a plurality of front units including transducer arrays having different frequency bands and different drive voltages, transmission drivers configured to supply drive voltages restricted correspondingly to the transducer arrays to transmit ultrasonic beams from the transducer arrays, and preamplifiers having frequency bands restricted correspondingly to the frequency bands of the transducer arrays configured to amplify reception signals outputted from the transducer arrays;
a middle unit connected to a front unit selected according to an intended diagnosis from the plurality of front units and including an A/D converter configured to convert reception signals amplified in the selected front unit into a digital signal, a reception signal processor configured to frequency-modulate the digital signal obtained through conversion by the A/D converter to a baseband frequency, and a parallel/serial, converter configured to serialize the signal that is frequency-modulated by the reception signal processor, an input device performing input operation into the ultrasound diagnostic apparatus to operate the ultrasound diagnostic apparatus, and a display unit displaying information regarding the selected front unit;
a connector detachably connecting the selected front unit and the middle unit; and a back unit connected to the middle unit by wireless communication and configured to generate an ultrasound image based on reception signals amplified in the selected front unit, wherein by selecting the front unit according to the intended diagnosis from the plurality of front units and connecting the selected front unit to the middle unit through the connector, a change to a transducer array having a restricted frequency band for the intended diagnosis and a change to a transmission driver and a preamplifier corresponding to the transducer array are made.

2. The ultrasound diagnostic apparatus according to claim 1, wherein each of the plurality of front units and the middle unit further comprise dedicated CPUs and the connector includes a reception signal line for transmitting reception signals amplified in the selected front unit and a communication line for transmitting signals between both CPUs of the selected front unit and the middle unit.

3. The ultrasound diagnostic apparatus according to claim 2, wherein the plurality of front units further comprise multiplexers connected to the transducer arrays.

4. The ultrasound diagnostic apparatus according to claim 3, wherein each of the transducer arrays of the plurality of front units comprises a transmission transducer array dedicated to transmission and a reception transducer array dedicated to reception.

5. The ultrasound diagnostic apparatus according to claim 4, wherein the middle unit further comprises an A/D converter configured to convert reception signals amplified in the selected front unit into a digital signal, a reception signal processor configured to frequency-modulate the digital signal obtained through conversion by the A/D converter to a baseband frequency, and a parallel/serial converter configured to serialize the signal that is frequency-modulated by the reception signal processor.

6. The ultrasound diagnostic apparatus according to claim 3, wherein each of the transducer arrays of the plurality of front units comprises a dual-purpose transducer array for transmission and reception and a harmonic transducer array for harmonic component reception.

7. The ultrasound diagnostic apparatus according to claim 6, wherein the middle unit further comprises an A/D converter configured to convert reception signals amplified in the selected front unit into a digital signal, a reception signal processor configured to frequency-modulate the digital signal obtained through conversion by the A/D converter to a baseband frequency, and a parallel/serial converter configured to serialize the signal that is frequency-modulated by the reception signal processor.

8. The ultrasound diagnostic apparatus according to claim 3, wherein the middle unit further comprises an A/D converter configured to convert reception signals amplified in the selected front unit into a digital signal, a reception signal processor configured to frequency-modulate the digital signal obtained through conversion by the A/D converter to a baseband frequency, and a parallel/serial converter configured to serialize the signal that is frequency-modulated by the reception signal processor.

9. The ultrasound diagnostic apparatus according to claim 2, wherein each of the transducer arrays of the plurality of front units comprises a transmission transducer array dedicated to transmission and a reception transducer array dedicated to reception.

10. The ultrasound diagnostic apparatus according to claim 2, wherein each of the transducer arrays of the plurality of front units comprises a dual-purpose transducer array for transmission and reception and a harmonic transducer array for harmonic component reception.

11. The ultrasound diagnostic apparatus according to claim 2, wherein the middle unit further comprises an A/D converter configured to convert reception signals amplified in the selected front unit into a digital signal, a reception signal processor configured to frequency-modulate the digital signal obtained through conversion by the A/D converter to a baseband frequency, and a parallel/serial converter configured to serialize the signal that is frequency-modulated by the reception signal processor.

12. The ultrasound diagnostic apparatus according to claim 1, wherein each of the transducer arrays of the plurality of front units comprises a transmission transducer array dedicated to transmission and a reception transducer array dedicated to reception.

13. The ultrasound diagnostic apparatus according to claim 1, wherein each of the transducer arrays of the plurality of front units comprises a dual-purpose transducer array for transmission and reception and a harmonic transducer array for harmonic component reception.

* * * * *